(12) United States Patent
Becker

(10) Patent No.: US 8,202,317 B2
(45) Date of Patent: Jun. 19, 2012

(54) SELF SUPPORTING AND FORMING BREAST IMPLANT AND METHOD FOR FORMING AND SUPPORTING AN IMPLANT IN A HUMAN BODY

(76) Inventor: Hilton Becker, Boca Raton, FL (US)

( * ) Notice: Subject to any disclaimer, the term of this patent is extended or adjusted under 35 U.S.C. 154(b) by 305 days.

(21) Appl. No.: 12/552,353

(22) Filed: Sep. 2, 2009

(65) Prior Publication Data

US 2011/0054604 A1    Mar. 3, 2011

(51) Int. Cl.
*A61F 2/12* (2006.01)
*A61F 2/00* (2006.01)

(52) U.S. Cl. .................. 623/8; 600/37
(58) Field of Classification Search .......... 623/7–8; 600/37
See application file for complete search history.

(56) References Cited

U.S. PATENT DOCUMENTS

| | | | |
|---|---|---|---|
| 4,648,880 A | | 3/1987 | Brauman |
| 5,522,896 A | * | 6/1996 | Prescott ............ 623/23.56 |
| 5,584,884 A | * | 12/1996 | Pignataro ............ 623/8 |
| 5,716,408 A | * | 2/1998 | Eldridge et al. .......... 606/213 |
| 6,210,439 B1 | * | 4/2001 | Firmin et al. ............ 623/8 |
| 6,432,138 B1 | | 8/2002 | Offray et al. |
| 6,666,893 B2 | | 12/2003 | Burg et al. |
| 6,913,626 B2 | | 7/2005 | McGhan |
| 7,476,249 B2 | * | 1/2009 | Frank ............ 623/8 |
| 7,875,074 B2 | * | 1/2011 | Chen et al. ............ 623/8 |
| 2002/0116070 A1 | * | 8/2002 | Amara et al. ............ 623/23.74 |
| 2007/0198085 A1 | | 8/2007 | Benslimane |
| 2008/0097601 A1 | * | 4/2008 | Codori-Hurff et al. ........ 623/8 |
| 2009/0163936 A1 | | 6/2009 | Yang et al. |
| 2009/0210056 A1 | | 8/2009 | Forsell |
| 2010/0016983 A1 | | 1/2010 | Smit |
| 2010/0094416 A1 | | 4/2010 | Maguire et al. |
| 2010/0217388 A1 | * | 8/2010 | Cohen et al. ............ 623/8 |
| 2011/0009960 A1 | * | 1/2011 | Altman et al. ............ 623/8 |
| 2011/0054605 A1 | * | 3/2011 | Becker ............ 623/8 |
| 2011/0106249 A1 | * | 5/2011 | Becker ............ 623/8 |

* cited by examiner

*Primary Examiner* — Suzette J Gherbi
(74) *Attorney, Agent, or Firm* — Cantor Colburn LLP

(57) ABSTRACT

A self supporting breast implant includes a generally cone shaped partially absorbable medical mesh support member and a silicone shell defining a hollow core that is preferably filled or partially filled with a silicone gel. The support member is made of a polypropolene/poliglecaprone monofilament and may be attached to a patient's tissue by sutures or by absorbable hooks.

11 Claims, 3 Drawing Sheets

SELF SUPPORTING AND FORMING BREAST IMPLANT AND METHOD FOR FORMING AND SUPPORTING AN IMPLANT IN A HUMAN BODY

FIELD OF THE INVENTION

This invention relates to a self supporting and self forming implant and to a method for forming and supporting a breast implant in a human body.

BACKGROUND FOR THE INVENTION

Implants for breast augmentation and/or reconstruction are well known and have been in use for over 20 years. During that period, the implants have undergone a number of significant changes. For example, early implants had a smooth outer shell; however, as developments progressed the smooth shell was replaced with a textured surface. This was done in an effort to reduce problems associated with capsular contraction and to support a natural or pear shaped implant in position.

One approach to the use of a textured surface is disclosed in my co-pending U.S. patent application Ser. No. 12/169,000 filed on Jul. 8, 2008, that is a Continuation-In-Part of U.S. patent application Ser. No. 12/026,032 filed on Feb. 5, 2008. As disclosed therein, a method for texturing the surface of a synthetic implant includes the steps of providing an implant having a textured outer layer of silicone elastomer having a plurality of cavities filled with tissue growth enhancing material. Portions of the tissue growth enhancing materials protrude outwardly from the filled cavities. The implant also includes a hollow core filled with a fluid gel or liquid of silicone, saline or soy and a layer or mass of a biologically active non-absorbable material such as non-absorbable acellular dermis. The method also includes the step of forming a capsular pouch from the mass of biologically active non-absorbable material, placing the implant into the pouch and implanting the pouch containing the implant behind the breast thus holding the implant in position and reducing capsular contraction by the surrounding tissue and blood and blood vessels growing into the acellular dermis. In a preferred embodiment of the invention the acellular dermis, collagen are combined with hyaluronic acid and partially impregnated in the outer layer of silicone elastomer so that the patient's blood vessels and tissue grow into the biologically active non-absorbable or only partially absorbable filled cavities to thereby anchor the implant in place.

Notwithstanding the above it is Applicant's belief that there is a need and a potential market for an improved textured surface implant and a method for breast implant reconstruction and augmentation in accordance with the present invention. There should be a need and a market for such implants because they provide better anchoring, shape enhancement and less problems with capsular contraction. Further, it is believed that such implants can be marketed at a competitive price, are durable, improve the rate of healing and lead to more satisfactory results.

BRIEF SUMMARY OF THE INVENTION

In essence a self supporting breast implant for breast augmentation and/or reconstruction comprises and/or consists of a generally cone shape support and an implant disposed within the support. In a preferred embodiment of the invention, the support is formed from a sheet of ULTRAPRO® partially absorbable light weight surgical mesh consisting of about 75% polypropylene (non-absorbable) and 25% poliglecaprone (absorbable) monofilament materials, available from Ethicon Inc., a Johnson and Johnson company located in Langhorne, Pa. In practice, a disc shaped piece of mesh has a triangular piece removed and the edges left by the removal of the triangular piece are joined together to form a three dimensional cone shaped support. The implant comprises a silicone shell, a hollow core and a silicone or saline fluid dispersed in the hollow core. The implant is placed within the cone and because of the flexibility of the mesh forms a generally pear or naturally shape of a breast. The mesh also includes means such as an overlap of the mesh material for suturing to a patient's tissue or in the alternative including two or three absorbable hooks.

The invention also contemplates a method for forming and supporting a breast implant including the steps of providing a breast implant and a mass of partially absorbable light weight surgical mesh. The surgical mesh is formed into a generally cone shaped support and the implant, a smooth sided, non-absorbable shell is disposed in the cone shaped support. In a preferred embodiment of the invention the base of the cone is enclosed with a sheet of the mesh material so that the implant, preferably having a smooth surface, is fully covered by the mesh support that is in close proximity thereto and the mesh support or an extension thereof is surgically attached to the patient's tissue to thereby provide an internal bra-like support. Also, because of the flexibility of the mesh material, the cone shaped mesh in combination with the generally round or slightly pear shaped implant takes on the natural form of a breast. Ideally the mesh support pouch is used with an adjustable implant. With an adjustable gel implant, the implant can be expanded to further enhance the shape.

The invention will now be described in connection with the following drawings wherein like numbers have been used to identify like parts.

DESCRIPTION OF THE PREFERRED EMBODIMENTS OF THE INVENTION

Figure 1:
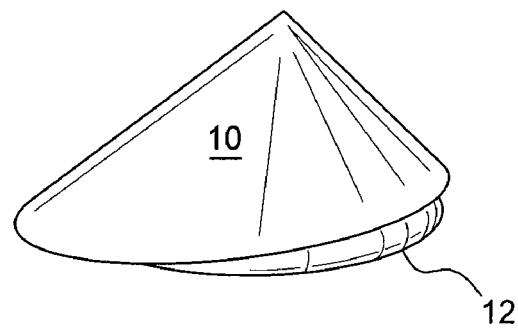
FIG. 1 is a schematic illustration of a generally cone shaped support.

As illustrated in FIG. 1 a generally cone shaped support member 10 is formed from a mass or sheet of medical mesh as for example ULTRAPRO®, partially absorbable material from Ethicon Inc., a Johnson and Johnson company located in Langhorne, Pa. This mesh which is used in the preferred embodiment of the invention is constructed of polypropylene, about 75% (non-absorbable) and poliglecaprone, about 25% (absorbable), monofilament material.

The absorbable portion of the mesh may encompass the whole surface, or part of the surface i.e. the upper portion can be predominantly absorbable while the lower part is predominantly non absorbable, this will allow a sling of support to remain inferiorly while the upper portion is absorbed. The direction of the elasticity can also be configured so as to enhance shape of a round implant on expansion, i.e. if the anterior lower portion is made more elastic than the upper portion, a round implant will assume a pear shape It is contemplated that other synthetic meshes may be used as for example polypropolene mesh with filament diameters ranging from 0.08 mm to 0.20 mm, pore size from about 0.8 to 3.0 mm and weights from 25 to 100 grams per square meter. Other materials include polyester felt, polyester knitted mesh, polytetrafluoethylene, nylon, etc. In addition, various other types of mesh may be used in forming a support. For example, biological mesh made from collagen sheets of human and animal origin, synthetic woven mesh as for example nylon, Dacron, Gore-Tex and combination meshes with strands of nylon interwoven with strands of collagen.

The generally cone shaped support may be formed by taking a disc shaped piece of mesh and removing a triangular portion from the disc. The edges of the pie shape with a piece removed are then joined together to form a generally three dimensional cone shape as shown in FIG. 1. As shown, the cone shaped member 10 is placed on top of a silicone shell 12 that is filled with a silicone or saline fluid. In a preferred embodiment of the invention, the implant is fully enclosed in a bag like support that includes the cone shaped structure.

Figure 2:
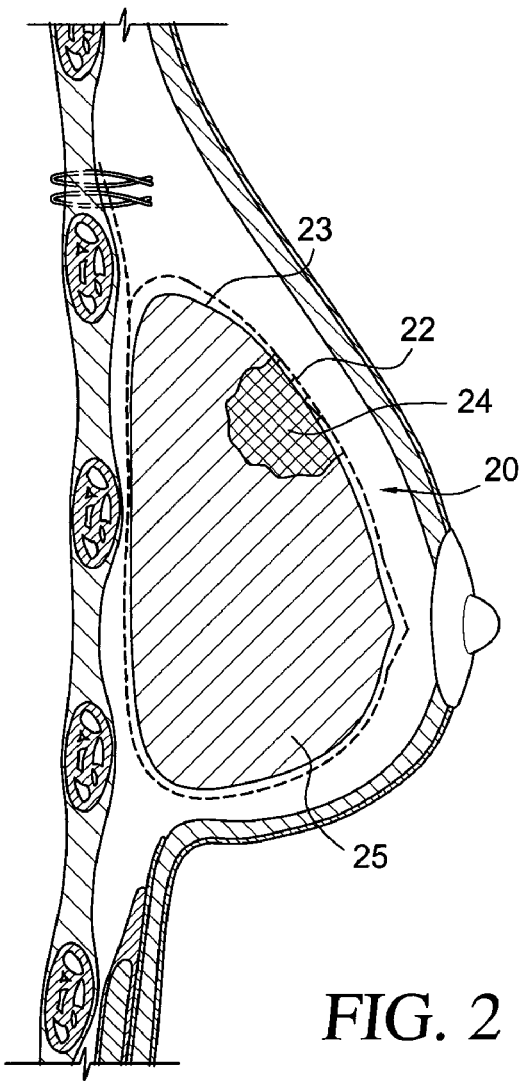
FIG. 2 is a schematic illustration of an implant dispersed in a mesh support in accordance with the present invention.
Figure 4:
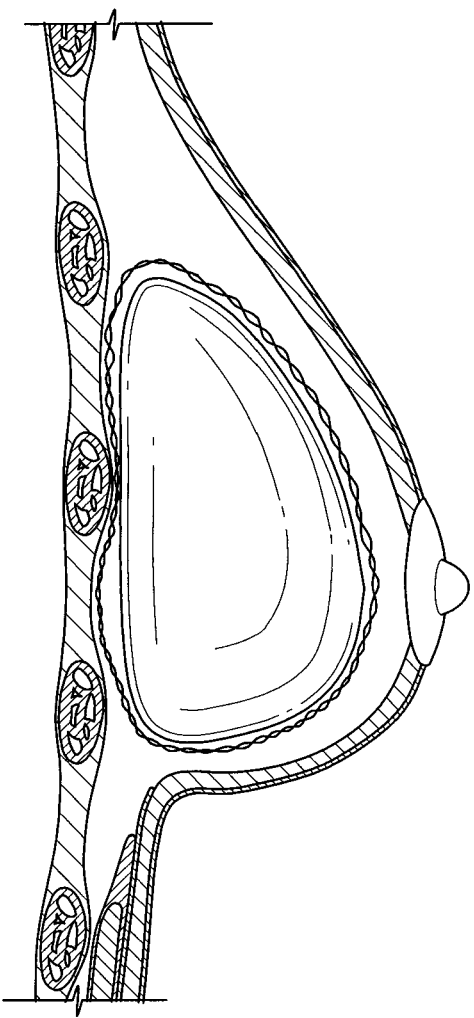
FIG. 4 is a cross-sectional view of a breast including a breast implant disposed therein in accordance with a preferred embodiment of the invention.
Figure 5:
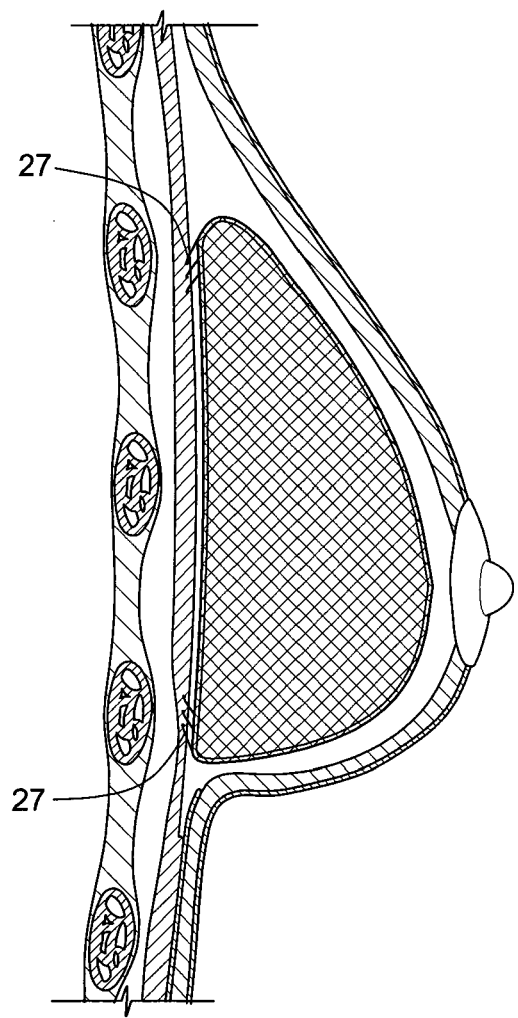
FIG. 5 is a schematic illustration of a implant with a mesh pouch enclosing the implant and including absorbable hooks in a rear portion thereof for attachment to a patient's tissue.

As shown in FIG. 2 an improved breast implant 20 in accordance with one embodiment of the invention includes a mesh pouch 22 of a light weight partially absorbable monofilament material and a non-absorbable silicone shell 23 that defines a hollow core 24 that is filled with silicone gel 25 or the like. The implant also includes an extension 26 of the mesh pouch 22 that is sutured to a patient's tissue. The implant includes a tube (not shown) leading to the pouch, but held within the surgeons hand. The remote port and tube are of conventional design and typically used to insert additional saline or silicone fluid or reduce the fluid filler from the inner prosthesis. The inner non-absorbable prosthesis or implant 23 is shown in FIGS. 4 and 5 wherein the inner prosthesis or inner implant 23 is encased in the mesh pouch 22. The mesh pouch is closed in an upward portion 25 to provide a fully enclosed structure.

Figure 3:
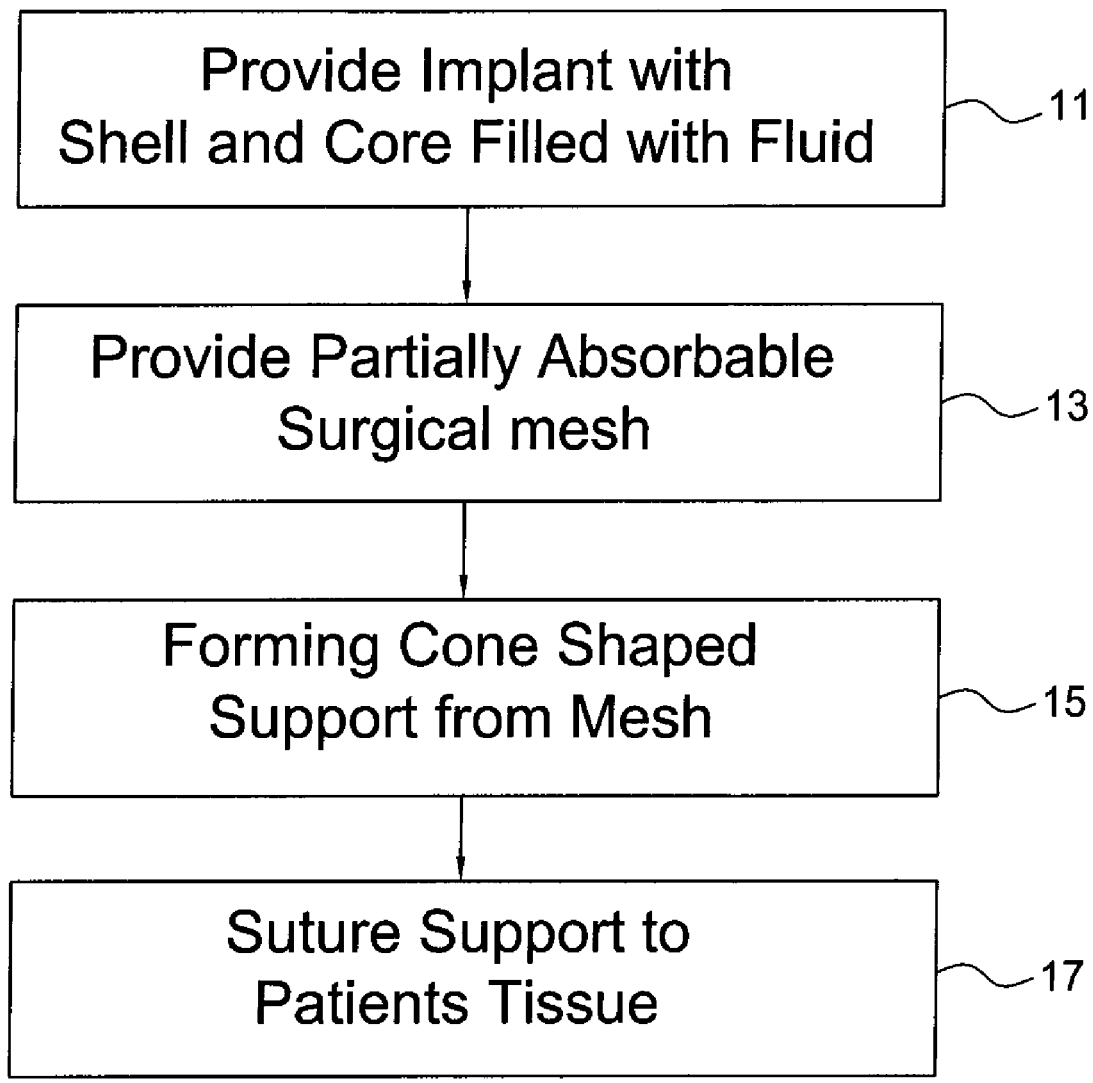
FIG. 3 is a flow chart illustrating a method for forming and supporting a breast implant in accordance with the present invention.

As illustrated in FIG. 3 a method in accordance with the present invention contemplates the following steps: The method includes the step 11 of providing an implant with an outer shell of medical grade silicone or the like having an inner core that is filled with a silicone gel, saline, etc. The method also includes the step 13 of providing a partially absorbable surgical mesh that is formed into a cone-shaped support in step 15 that is subsequently attached to a patient's tissue in step 17.

In FIG. 4, the pouch 22 is slightly spaced from the outer shell 23 in a manner that appears to minimize problems associated with capsular contraction.

It is also contemplated that rather than stitching the implant to the patient's tissue, the implant may be readily attached by a plurality of absorbable hooks 27 as shown in FIG. 5.

While the invention has been described in connection with its preferred embodiments, it should be recognized that changes and modifications may be made therein without departing from the scope of the appended claims.

What is claimed is:

1. A self supporting breast implant comprising a three dimensional cone shaped mesh support having a flat bottom and a breast implant comprising a synthetic shell, a hollow core and a mass of silicone or saline fluid or gel disposed within said cone shaped support and wherein said cone shaped support includes attachment means for attaching said support to a patient's tissue without piercing the said implant.

2. A self supporting breast implant according to claim 1 in which said cone shaped support includes a relatively flat back surface attached to a base of said cone shaped support.

3. A self supporting breast implant according to claim 2 in which said breast implant has a smooth surface enclosed within said mesh support.

4. A self supporting breast implant according to claim 3 in which there is a slight distance between said breast implant and said mesh support.

5. A self supporting breast implant according to claim 3 in which said implant is made of silicone.

6. A self supporting breast implant according to claim 4 in which said implant is a multi-lumen implant round or pear shaped.

7. A self supporting breast implant according to claim 5 in which said mesh comprises a lightweight partially absorbable monofilament material.

8. A self supporting breast implant according to claim 7 in which said mesh consists of about 75% polypropylene and 25% poliglecaprone monofilament material.

9. A method for forming a support for a breast implant comprising the steps of:
   providing a breast implant and a mass of surgical mesh;
   forming a generally cone shaped mesh support; and
   attaching said mesh support to a patient's tissue without penetrating the implant.

10. A method for forming and supporting a breast implant, said method consists of the following steps:
   providing a silicone breast implant having a silicone elastomer shell including an outer layer of smooth silicone elastomer, a hollow core and a silicone or saline fluid or gel dispersed within said hollow core;
   a mass of a light weight partially absorbable flexible monofilament materials; forming a cone shape support member from said monofilament materials;
   placing the breast implant within the cone shaped support member with a flat bottom and closing said support member about said implant; and
   attaching the support member to a patient's tissue without penetrating the implant.

11. A self supporting breast implant for breast augmentation consisting of:
   a three dimensional cone shaped mesh support having a flat bottom made of about 75% polypropylene and 25% poliglecaprone monofilaments;
   a silicone elastomer shell including a smooth outer surface layer of
   silicone elastomer, a hollow core and silicone or saline fluid or gel dispersed with said hollow core; and
   wherein said cone shaped support includes attachment means wherein said attachment means are absorbable hooks fixed to a rear portion of said mesh pouch.

* * * * *